Figure 1:
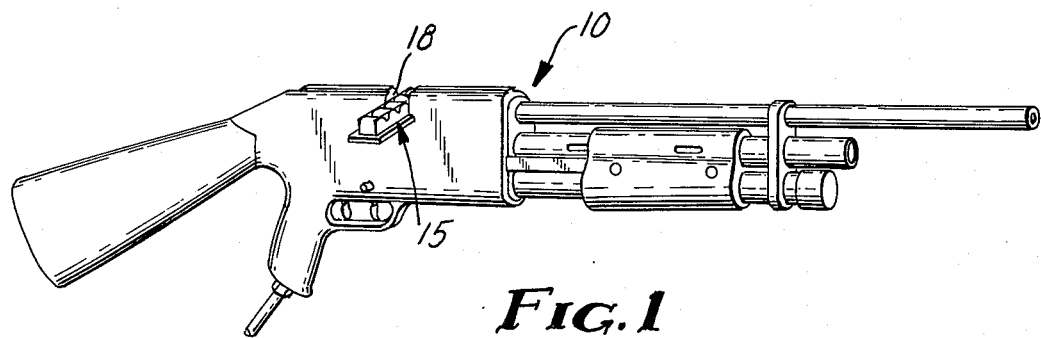
Figure 2:
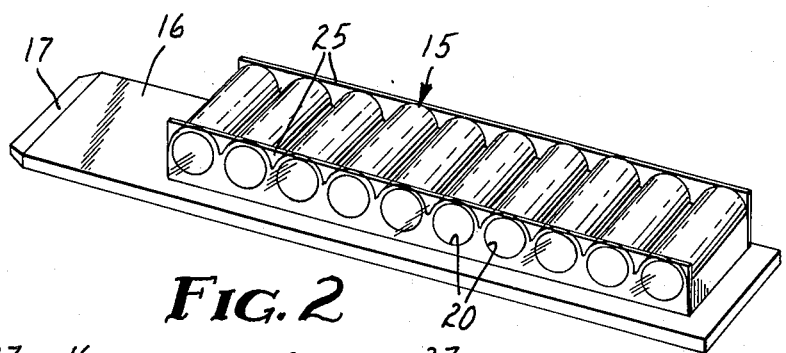
Figure 3:
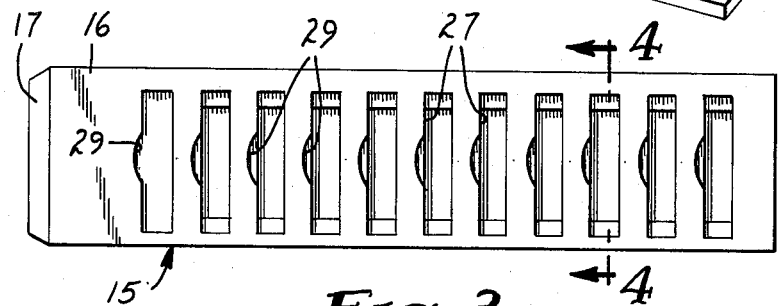
Figure 4:
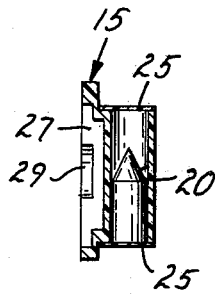

United States Patent [19]

Fischer et al.

[11] 4,004,565
[45] Jan. 25, 1977

[54] CLIP FOR SUPPLYING IMPLANT PROJECTILES

[75] Inventors: Earl Lee Fischer, Bentonville, Ark.; Jay W. Gould, III, Bloomington, Minn.

[73] Assignee: Minnesota Mining and Manufacturing Company, St. Paul, Minn.

[22] Filed: Apr. 14, 1975

[21] Appl. No.: 567,495

[52] U.S. Cl. .................. 124/45; 273/DIG. 4; 273/DIG. 9; 206/534; 206/532; 206/471; 128/217

[51] Int. Cl.² ................................. F41C 25/00

[58] Field of Search .................. 124/45, 1; 206/366, 206/3, 461, 471, 531, 532, 534; 128/217; 89/35 R; 102/92; 85/17; 273/106.5 D, 106.5 R, DIG. 4, DIG. 9; 119/156

[56] References Cited

UNITED STATES PATENTS

| | | | |
|---|---|---|---|
| 3,472,367 | 10/1969 | Hellstrom | 206/534 X |
| 3,520,299 | 7/1970 | Lott et al. | 128/217 |
| 3,706,260 | 12/1972 | Rausing | 89/35 R |
| 3,774,607 | 11/1973 | Schmitz | 128/217 |

*Primary Examiner*—Richard C. Pinkham
*Assistant Examiner*—William R. Browne
*Attorney, Agent, or Firm*—Alexander, Sell, Steldt & DeLaHunt

[57] ABSTRACT

A clip for use with a gas-operated gun to package and supply to the gun hygienic projectiles for inoculating animals with a particular biologically active material. The clip contains a molded structure having a plurality of axially aligned adjacent cylindrical chambers receiving the implant projectile and each chamber is sealed by a rupturable sealing film at each end thereof. Indexing recesses are provided on said structure and associated with each of the chambers for indexing the clip in the gun to dispose seriatim the chambers in alignment with the bore of the gun.

18 Claims, 6 Drawing Figures

U.S. Patent  Jan. 25, 1977  4,004,565

CLIP FOR SUPPLYING IMPLANT PROJECTILES

BACKGROUND OF THE INVENTION

1. Field of the Invention

This invention relates to an improved clip for supplying implant materials to an instrument for implanting the same and in one aspect to a combined package and clip having sealed rupturable chambers containing hygienic ballistic implant projectiles and recesses for indexing the chambers in a gun.

2. Description of the Prior Art

Prior art devices are known for subcutaneous implant of pellets into animals. In most instances these devices utilize a structure wherein the dispensing gun includes a needle point on the barrel, which needle is inserted into the animal and subsequent operation of the gun will implant the pellets under the skin of the animal. The pellets for these implant guns are provided in magazines and the known magazines are merely circular holders and do not provide sealed packaging for the pellets. Examples of these known devices are disclosed in U.S. Pat. No. 3,520,299, issued July 14, 1970 to J. A. Lott et al; U.S. Pat. No. 3,669,104, issued June 13, 1972 to J. B. Wyatt et al; and U.S. Pat. No. 3,774,607, issued Nov. 27, 1973 to S. W. Schmitz.

It is very advantageous however to be able to fire a projectile at some distance from an animal to afford the implant and to package the implant projectile in such a manner that each projectile contains a separate dose of a biologically active material for inoculation. The clip of this invention protects each projectile within a cavity or chamber by a rupturable seal from impurities, providing a hygienically packaged projectile with the biologically active material in the dry form preventing contamination, or loss of potency, i.e. strength.

The clip is structured to permit individual injection and then removal of the clip without disturbing the hydgienic packaging of the remaining implant projectiles.

The advantages of the clip of the present invention is to afford a refrigeratable package for each individual measured inoculation to maintain the biologically active material in a stable form until the inoculation occurs. The clip may be refrigerated if necessary and merely removed and placed in the gun and individual, or successive, inoculations may take place.

By the use of implant projectiles individually packaged as provided by the present invention, each animal receives a measured dose and there is no danger of contamination by the inoculating device being used on successive animals causing contamination of one animal from a first contaminated animal.

Each implant projectile of the present invention is individually sealed in the clip and is not touched after it is originally packaged.

Individual inoculations are possible without reconstituting and possibly contaminating or destroying more of the dry vaccine than is needed at any one time. The projectiles are protected from contaminants such as dirt, bacteria etc. until placed in the barrel of a gun.

The convenience of using implant projectiles which may be placed into a gun and discharged at some distance is great in that there is no need to capture, corral or otherwise restrain the animal during the inoculation.

A further direct advantage to the user is that there is no need to touch or get next to the contaminated animal which may have a highly contagious disease.

SUMMARY OF THE INVENTION

This invention is directed to a clip for insertion into a gas-operated gun which clip is the package for hygienic ballistic implant projectiles containing a biologically active material. The clip comprises a molded structure having therein a plurality of spaced chambers on parallel axes and indexing means associated with the chambers. A ballistic implant projectile containing a biologically active material is placed in each of said chambers and a rupturable sealing means seals each end of each of said chambers to individually isolate each of said chambers from the ambient environment. The molded structure has a rectangular web with the chambers positioned transversely on one surface and with the indexing means defined by recesses on the opposite surface.

DESCRIPTION OF THE DRAWING

The foregoing will be more fully understood after reading the following description which refers to the accompanying drawings wherein:

FIG. 1 is a perspective view of a gas-operated gun and the clip of the present invention;

FIG. 2 is a perspective view of the clip of the present invention;

FIG. 3 is a bottom view of the clip of FIG. 2;

FIG. 4 is a sectional view taken on the line 4—4 of FIG. 3;

FIG. 5 is a plan view of the clip of FIG. 1 with portions thereof in section; and FIG. 6 is a side view of the clip of FIGS. 2 through 5 showing the clip with portions thereof in section.

DESCRIPTION OF THE PREFERRED EMBODIMENT

The present invention relates to an improved clip for use with a gun to implant projectiles in animals. The clip not only forms a part of the implant instrument but is also an aseptic package for the implant projectiles containing a biologically active material which projectile may be used for inoculating animals by the nonlethal implantation of the projectile totally within a living animals. Following implantation, the biologically active material is released in situ in the animal in response to interaction with the fluids and cells in the animal body.

The gun, generally designated 10, is adapted to receive the clip generally designated 15 to permit the implantation of a ballistic projectile with sufficient velocity to penetrate the epidermal covering of a living animal body and lodge totally within the body. The projectile will then present a biologically active material to the living body which material is released and assimilated by the body fluids and cells surrounding the implanted projectile.

The clip 15 provides an aseptic package for protecting and then delivering a predetermined measured dosage of a biologically active material in a concentrated, freeze-dried form which will not be contaminated or diluted or subjected to other deleterious affects prior to the desired use of the projectile.

The clip 15 of the present invention comprises a molded structure including a web 16 which is generally rectangular in shape having at one end a tapered edge 17 to facilitate the insertion of the clip into a transverse guide passage 18 in the housing of the gun 10. On one surface of the web 16 and molded integrally therewith is a plurality of transversely positioned, equally spaced cylindrical chambers 20 having parallel axes. Each of the chambers have opposite open ends and are formed with connected wall structures to make the structure more rigid. The chambers 20 are placed in a row along the web. One end of each chamber is closer to one edge of the web than the opposite end for purposes of registration within the gun 10 and one end of the row is spaced from said tapered edge 17 to provide a tongue on the clip.

Within each of the chambers 20 on the web 16 is a ballistic implant projectile 22. The projectile 22 comprises a conical nose and annular walls defining a generally cylindrical body which may have a cavity containing the biologically active material. The projectile 22 can be made of any material which is capable of being projected with sufficient force to penetrate a living animal body and which will maintain its integrity, e.g., will not shatter, on impacting and entering the animal body. Any of the numerous biomedically approved plastics can be used with advantage and can be selected from among those which are either soluble or insoluble in the animal body. Exemplary of useful insoluble materials are the synthetic organic polymers such as the polyolefins, e.g., polyethylene and polypropylene; polysiloxane; polyamides, such as nylon; fluorinated hydrocarbon resins; ABS polymers (acrylonitrile butadiene-styrene polymers) and the like. A suitable class of polymers which are soluble in animal bodies, e.g. cattle, are the cellulose derivatives such as hydroxypropyl cellulose, available commercially from the Hercules Powder Co. under the trademark "Klucel". The use of soluble projectiles can be particularly advantageous since after implant the projectile will be solubilized in and eliminated from the animal's body, eliminating the need to retrieve the projectile.

The projectile 22 may be a 25 calibre projectile and the nose cone and the cavity opening to the rear of the projectile is loaded with a given dose of biologically active material. The biologically active material may include antigens, tranquilizers, vitamins, narcotics etc. Bacterial cells or extracts may be added to the antigen preparations as adjuvants to provoke an increased immune response. The antigens should include materials which when administered to an animal will cause the formation of antibodies by the animal, such as the viruses, bacteria, and toxoids are well known in the art, and would be useful in the practice of this invention. Narcotics may be administered to narcotize the animal.

Figure 6:
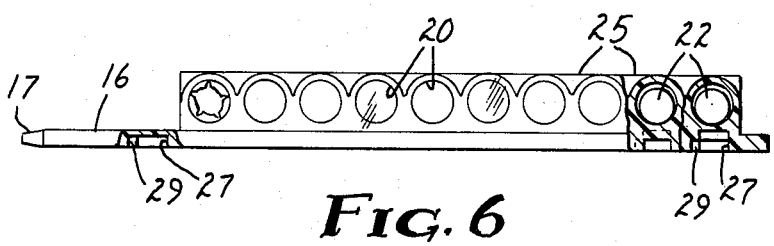

On the other surface of the molded structure are spaced transversely extending recesses 27. The recesses 27 are indexing means and are positioned in corresponding spaced relation to the chambers 20 for positioning an associated chamber in aligned relationship to the barrel of the gun. There is one more recess, as shown most clearly in FIG. 6 than there are chambers to index the clip initially in the gun 10 before the bolt is operated. Each of the recesses 27 is formed by walls disposed to form a rectangularly shaped portion for receiving a spring-biased detent and the leading edge wall of each rectangular recess is provided with an arcuate wall portion 29 to receive and position a circular pawl to advance the clip transversely of the housing of the gun 10 to successively align each of the chambers 20 with the barrel of the gun 10.

Each of the chambers 20 is sealed by a mechanically rupturable seal at each end to protect and aseptically package the projectile. To protect the projectile means to exclude from the chambers contaminates such as dirt, bacteria etc., the chambers are sealed in a preferred embodiment by placing a sealing film 25 along the open end of the chambers and bonding the sealing film to the material of the clip defining the chambers at each of the open ends to individually seal each chamber at each end. The films 25 are preferably a laminate of 0.5 (0.0254 mm) mil polyester and 1.5 mil polyethylene. The polyethylene surface is heat sealed to the molded structure to form a good impermeable bond with the molded structure around each chamber opening. The clip preferably is formed of a translucent high density polyethylene permitting the heat sealing of the film thereto.

If it is desired that the chambers be hermetically sealed to exclude penetration by gases and moisture the sealing means should include an impermeable material such as heat sealable aluminum foil and the clip should be made of a plastic impermeable to gas and moisture, e.g., a polyformaldehyde resin. The clip alternatively could be formed of injection moldable polyolefins or polyamides and other sealing films may be used.

Figure 5:
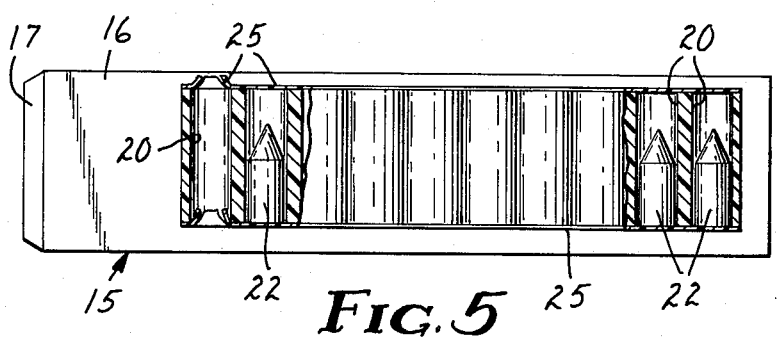

In operation, the breech of the gun has an obturator which penetrates the sealing means at one end of a chamber 20 aligned with the bore. The obturator then engages the projectile 22 forcing it to rupture the sealing film at the opposite end of the chamber and the obturator extends through the chamber forcing the projectile into the bore of the gun. FIG. 5 illustrates a clip 15 where the sealing film is ruptured on one chamber at the lead end and the projectile has been spent or fired from the gun. The clip can then be removed until another implant is desired and the remaining chambers remain aseptically sealed.

While the preferred form of the fire arm for launching or "shooting" the projectile into the animal uses compressed gas, preferably air, it is understood that the gun may use other launching devices such as an expanded gas similar to explosive charges.

The projectiles useable in this clip are described in copending applications assigned to the assignee of this application and are identified as Drake and Paul, Ser. No. 497,462, filed Aug. 14, 1974, now U.S. Pat. No. 3,948,263, issued Apr. 6, 1976; and Krogseng and Paul, Ser. No. 524,121, filed Nov. 15, 1974, now U.S. Pat. No. 3,982,536, issued Apr. 28, 1976.

The molded structure is preferably translucent to permit inspection of the projectiles which are formed of material having a distinct color, preferably not including the reds, to color code various biologically active materials. This coding avoids possible confusion when implanting different materials at substantially the same period of time.

Having described the invention what is claimed is:

1. A clip for hygienic ballistic implant projectiles containing a biologically active material comprising:
a rectangular structure having a plurality of chambers with parallel axes and indexing means associated with each of said chambers for use in registering said chambers in a gun and indexing the chambers seriatim,
ballistic implant projectiles containing a biologically active material positioned in said chambers, and
mechanically rupturable sealing means at each end of each of said chambers for individually isolating each of said chambers from the ambient environment and so that a device may penetrate the sealing means at one end of a chamber and force the projectile through the sealing means and out the chamber at the other end of the chamber.

2. A clip according to claim 1 wherein said structure is formed of polyethylene.

3. A clip according to claim 2 wherein said sealing means comprises a film bonded to said structure around each end of each chamber.

4. A clip according to claim 3 wherein said film is a laminate of polyethylene and polyester.

5. A clip according to claim 1 wherein said structure is formed of a gas and moisture impermeable material and said sealing means comprises a rupturable metal foil bonded to said structure around the end of each chamber.

6. A clip according to claim 5 wherein said material comprises a polyformaldehyde resin.

7. A clip according to claim 1 wherein said structure comprises a web having said chambers positioned on one surface transversely thereof and said indexing means comprises recesses formed in the opposite surface with one recess associated with each of said chambers.

8. A clip according to claim 7 wherein said web has a tapered edge at one end.

9. A clip according to claim 8 wherein said chambers are spaced from said one end to define a tongue to assist insertion of the clip in a gun.

10. A clip according to claim 7 wherein said sealing means is a laminate of polyester and polyethylene.

11. A clip according to claim 10 wherein said sealing means is a film said film is heat sealed to said structure at each end of each of said chambers.

12. A clip according to claim 7 wherein the structure is formed of polyethylene and said sealing means comprises a laminate of polyethylene and polyester heat sealed to said structure to cover and aseptically seal each end of each chamber.

13. A clip according to claim 7 wherein said chambers are cylindrical and are positioned in side-by-side relationship with each chamber having a common wall with at least one other chamber.

14. A clip according to claim 7 wherein each projectile has a conical nose and a generally cylindrical body and a cavity containing a biologically active material selected from the group consisting of antigens, vitamins, narcotics and tranquilizers.

15. A clip according to claim 7 wherein each projectile is formed of a material soluble in animal bodies.

16. A clip according to claim 6 wherein said structure is formed of a transparent polyformaldehyde resin and said sealing means comprises an aluminum foil heat sealed to said structure and covering each end of each chamber.

17. A clip according to claim 1 wherein each projectile has a conical nose and a generally cylindrical body and a cavity containing a biologically active material selected from the group consisting of antigens, vitamins, narcotics and tranquilizers.

18. A clip according to claim 1 wherein each projectile is formed of a material soluble in animal bodies.

* * * * *